US00PP29727P3

(12) United States Plant Patent
Infante

(10) Patent No.: US PP29,727 P3
(45) Date of Patent: Oct. 9, 2018

(54) NECTARINE TREE NAMED 'ANDES NEC-2'

(50) Latin Name: *Prunus persica*
Varietal Denomination: Andes Nec-2

(71) Applicant: VIVEROS ASOCIADOS CHILE LTDA. (ANA Chile-Andes Nursery Association), Paine (CL)

(72) Inventor: Rodrigo Infante, Paine (CL)

(73) Assignees: UNIVERSIDAD DE CHILE, Santiago (CL); VIVEROS ASOCIADOS CHILE LIMITADA, Santiago (CL)

( * ) Notice: Subject to any disclaimer, the term of this patent is extended or adjusted under 35 U.S.C. 154(b) by 4 days.

(21) Appl. No.: 14/544,849

(22) Filed: Feb. 25, 2015

(65) Prior Publication Data

US 2015/0230373 P1 Aug. 13, 2015

Related U.S. Application Data

(63) Continuation of application No. 13/766,222, filed on Feb. 13, 2013.

(51) Int. Cl.
*A01H 5/08* (2018.01)

(52) U.S. Cl.
USPC ..... Plt./190

(58) Field of Classification Search
USPC ..... Plt./180, 187, 190
See application file for complete search history.

(56) References Cited

U.S. PATENT DOCUMENTS

PP5,480 P * 5/1985 Nakagawa ..... Plt./190
PP19,918 P2 4/2009 Bradford

OTHER PUBLICATIONS

AgroNoticias. The race for the Chilean peach. Feb. 15, 2011. untranslated. http://www.cropscience.bayer.cl/noticias/vernoticia.asp?id=2555. 2 pages.*
AgroNoticias. The race for the Chilean peach. Feb. 15, 2011. Translated. http://www.cropscience.bayer.cl/noticias/vernoticia.asp?id=2555. 2 pages.*
Rodrigo Infante et al., "'Andes-1': An Early-maturing Clingstone Peach Cultivar for Canning and Fresh Market", HortScience, vol. 46, No. 3, 2011, pp. 499-500.
AgroNoticias, "La Carrera por el durazno chileno", Crop Science / Chile, Feb. 15, 2011.
AgroNoticias, "The race for the Chilean peach", Crop Science / Chile, Feb. 15, 2011.

* cited by examiner

*Primary Examiner* — Susan McCormick Ewoldt
*Assistant Examiner* — Karen M Redden
(74) *Attorney, Agent, or Firm* — Greer, Burns & Crain, Ltd.

(57) ABSTRACT

A new and distinct variety of clingstone nectarine tree denominated 'Andes Nec-2' which is characterized by the fruit of which maturing a week after the 'August Red' nectarine that matures at the end of the harvest season. The variety has a slow pulp softening rate commencing during the last two weeks before the commercial harvest, therefore, delaying the harvest. This produces fruit with increased size and soluble solids content. The variety has a high postharvest life potential, and will maintain its initial sensory quality at low temperatures over a period of time. Its fruit is striped/solid red blush over a light yellow background color, with a round, symmetrical fruit shape.

3 Drawing Sheets

Latin name: *Prunus persica.*
Varietal denomination: Andes Nec-2.

BACKGROUND AND SUMMARY

The present invention relates to the discovery and the asexual propagation through grafting on 'Nemaguard' rootstock of a new variety of nectarine tree, *Prunus persica* denominated 'Andes Nec-2'. This new cultivar resulted from a controlled hybridization between the nectarine 'Flavortop' (♀) and the nectarine genotype 'A67-03' (♂) performed in 1999 at Paine, Metropolitan Region, Chile (latitude −33° 80'S, longitude −70° 66'S, altitude 508 m above sea level). This genotype was for the first time asexually propagated through grafting on 'Nemaguard' rootstock in the same field on 2001. The rootstock 'Nemaguard' is a chance seedling selected in 1959 by USDA, and it has never been patented.

DISTINCTIVE CHARACTERISTICS OF THE VARIETY

'Andes Nec-2' is a self-fertile, with semi erect plant growth, weak to medium vigor. The fruit is round, symmetrical, with a striped/solid red blush over a light yellow background color. The ripening period of 'Andes Nec-2' is one week after 'Red August', the fruit has higher soluble solids concentration and lower softening rate than 'August Red'. Compared with the male genitor ('A67-03'), 'Andes Nec-2' shows a firmer flesh, the fruit size is 30 to 40% higher than 'A67-03' and the ripening time of 'Andes Nec-2' is two weeks earlier than 'A67-03'. The female genitor 'Flavortop' nectarine (not patented) was developed in Fresno, Calif. in 1969, and it has not been subjected to any patenting process. 'Flavortop' nectarine is harvested in California from July 15$^{th}$ to July 30$^{th}$, and in Chile on January 20$^{th}$, and 'Andes Nec-2' at the end of February, 30 to 40 days after 'Flavortop'.

The genotype 'A67-03' (not patented) is a nectarine developed in our own breeding program and obtained through the cross of the old nectarine 'Venus' (not patented), and the landrace peach named 'Copiapo' (not patented).

The main feature of 'Andes Nec-2' is its slow pulp softening rate commencing during the last two weeks before the commercial harvest. This characteristic enables delaying the harvest, to increase the size of the fruit and soluble solids content without affecting their postharvest life potential. Secondly, it shows a high postharvest life potential, which can reach up to 50 days at 0° C. while maintaining its initial sensory quality. From a sensory point of view, this is a variety of medium to high acidity with a balanced sweetness/acidity ratio and in general an average sensory quality. The variety is not susceptible to "chilling injury" and therefore can be used for exporting to distant markets from the production zone. Market use of Andes Nec-2 is mainly for human consumption of fresh fruit.

BRIEF DESCRIPTION OF THE FIGURES

The drawings of the nectarine of the present variety are color photographs.

DETAILED BOTANICAL DESCRIPTION

Figure 1A:
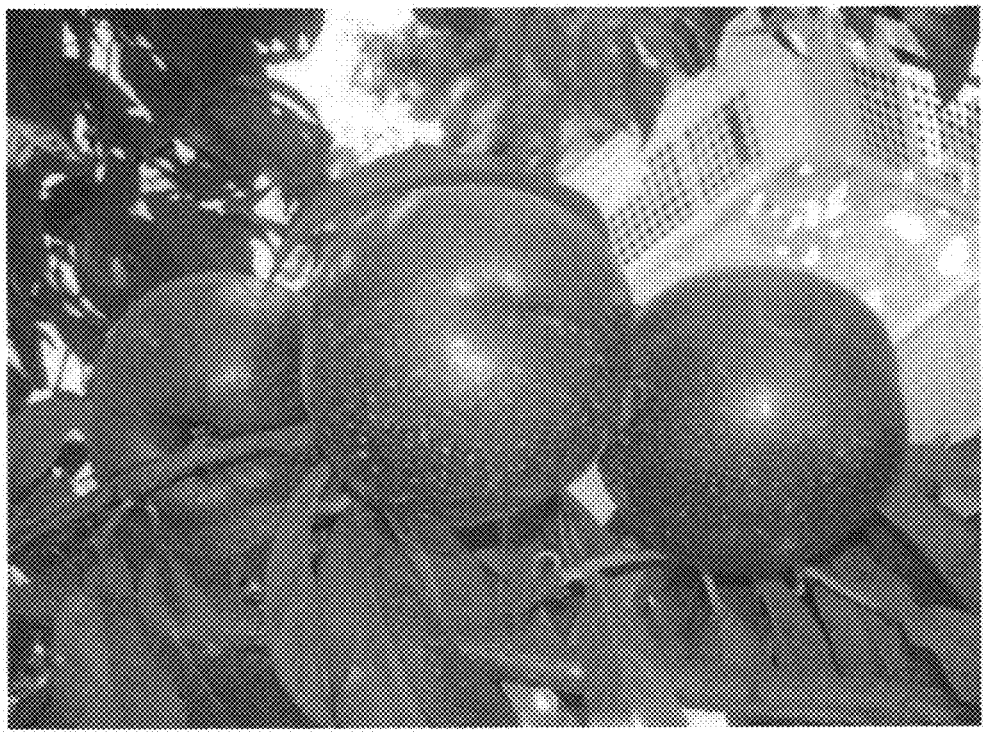
FIG. 1(*a*) and FIG. 1(*b*) show two views of the whole fruit in skin color and form, and typical leaves.
Figure 1B:
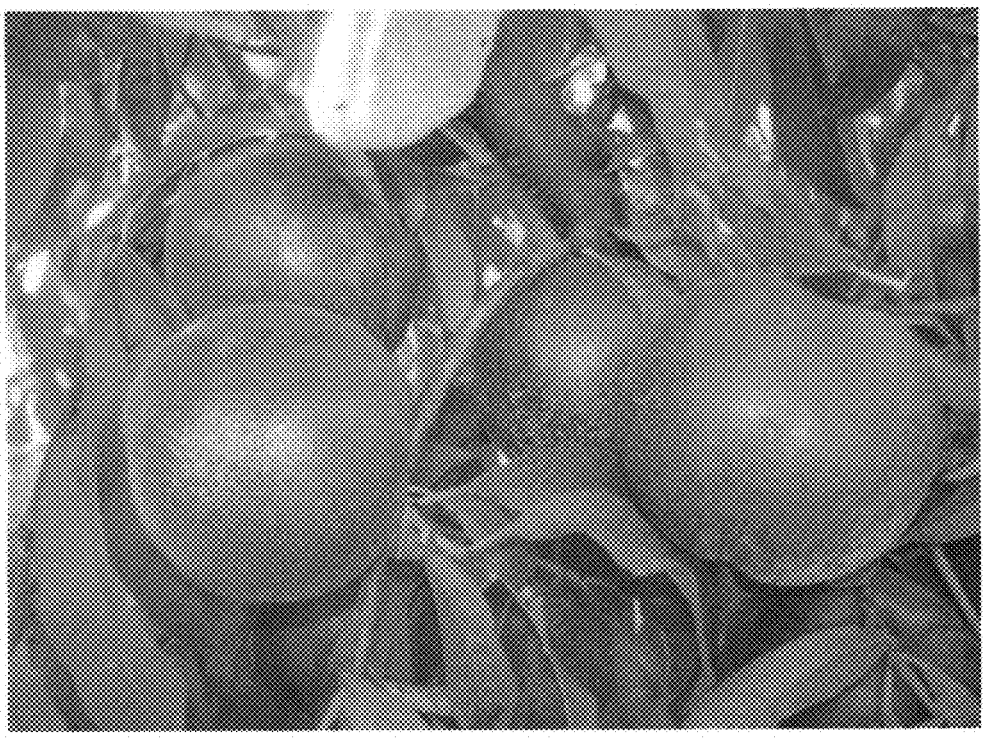
Figure 2:
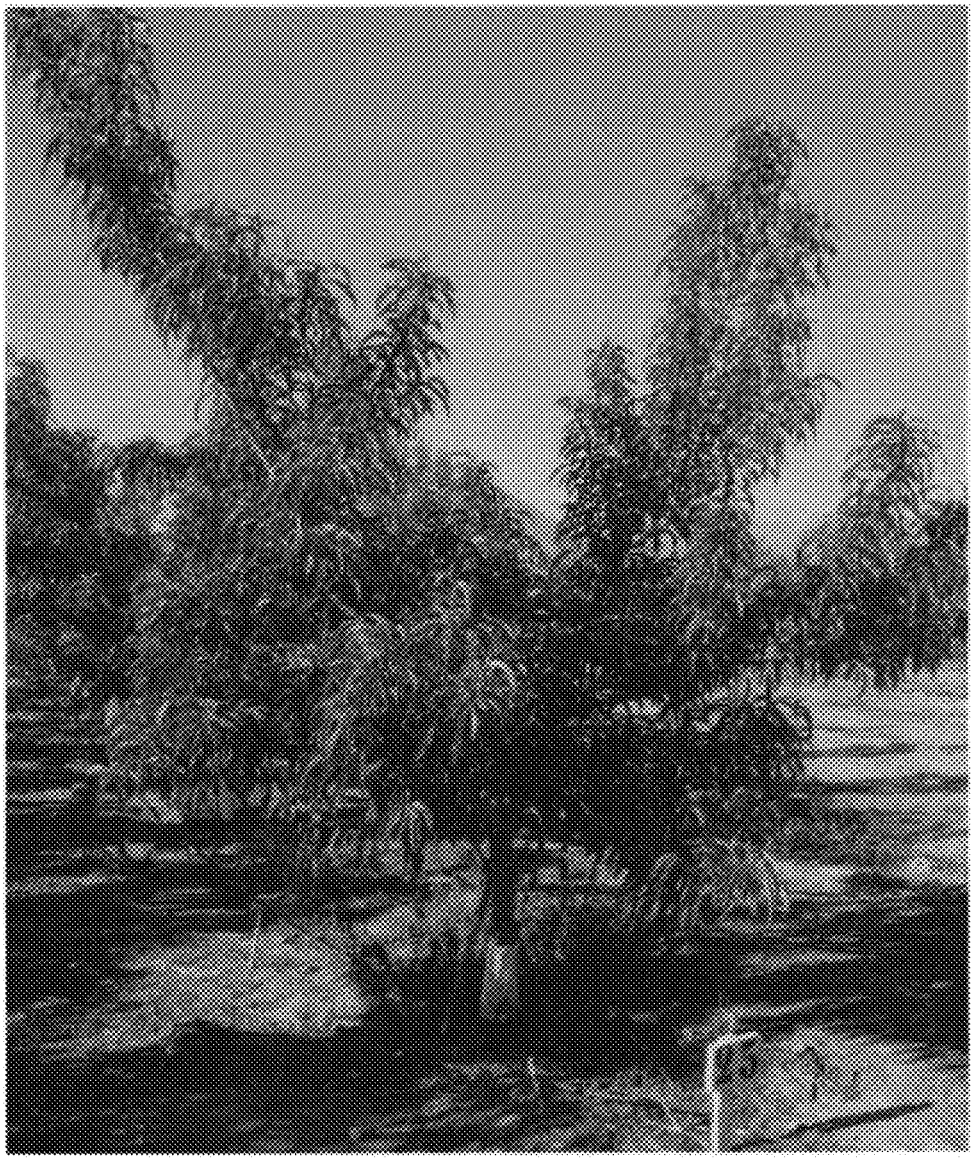
FIG. 2 shows a five year old tree of 'Andes Nec-2'.
Figure 3:
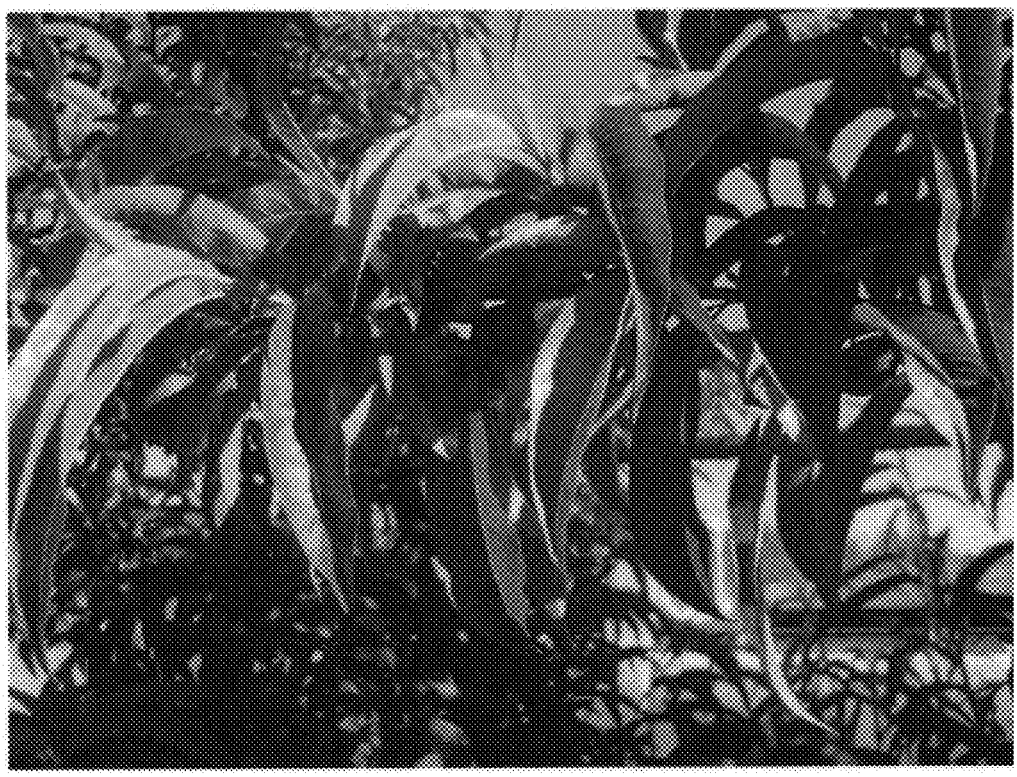
FIG. 3 shows branch of the tree of FIG. 2 and includes enlarged views of the upper surface of a leaf of 'Andes Nec-2'.

Tree:

1. *Size*.—Medium, 2.8-3.4 m high shaped as an open vase, 2.5-2.8 m diameter at the fifth year, similar to cultivar 'Robin' (not patented).
2. *Vigor*.—Medium, similar to cultivar 'J.H. Hale' (not patented). Shoots reach 30 to 50 cm on regular spring/summer growing period.
3. *Habit*.—Horizontal, like cultivar 'Albertina' (not patented). It is well adapted to open vase training.
4. *Flowering*.—Shoot thickness: Medium, 4.5-5.0 mm, similar to cultivar 'Redhaven' (not patented).
5. *Flowering shoot*.—Length of internodes: Medium, 5-8 cm, similar to cultivar 'Redhaven' (not patented).
6. *Flowering shoot*.—Anthocyanin coloration: Present. The shoot zone exposed to sunlight reach a light red color (color CIELab: L=29.00 a=52.50 b=22.21; is based on Mcguire R. G., 1992. Reporting of Objective Color Measurements, Hortscience 27: 1254-1255).
7. *Flowering shoot intensity of anthocyanin coloration*.—Weak, similar to cultivar 'Springtime' (not patented). The lower part of the shoot reaches a light brown color (color CIELab: L=26.40 a=3.37 b=7.51; Mcguire R. G., 1992).
8. *Flowering shoot*.—Density of flower buds (as for 4): Medium, similar to cultivar 'Michelini' (not patented), reaching in an average year 22-36 flowers/30 cm long shoot.
9. *Flowering shoot*.—General distribution of flower buds (as for 4): In groups of two or more, similar to cultivar 'Redhaven' (not patented). 10. The trunk of an 5-year old tree shows a 10-12 cm diameter, measured on 50 cm above the ground, the bark texture is smooth with few lenticels, and the bark color is dark brown (color CIELab: L=42.66 a=3.54 b=11.21; Mcguire R. G., 1992). The primary branches diameter reach 6-7 cm in an 5-year old tree, and the color is light brown (color CIELab: L=27.06 a=3.41 b=7.50; Mcguire R. G., 1992).
11. *Vegetative buds shape and color*.—Acuminate, 4.7-7.9 mm length, color brown (color CIELab: L=97.14 a=-6.78 b=28.63; Mcguire R. G., 1992).

Flower:

12. *Type*.—Showy, similar to cultivar 'Robin', reaching a whole diameter of 2.7 to 3.2 cm, and ovary is settled 0.5 to 0.6 cm low the calyx.
13. *Calyx*.—Color of inner side (opened flower, before falling of petals): Greenish yellow, similar to cultivar 'Robin' (not patented). The color is classified as (color CIELab L=62.01 a=14.08 b=25.67; Mcguire R. G., 1992).
14. *Corolla*.—Predominant color (inner side): Medium pink, similar to cultivar 'Fuzalode' (not patented), classified as CIELab: L=88.22 a=14.01 b=0.7; Mcguire R. G., 1992).
15. *Petal*.—Shape: Round, similar to cultivar 'Springtime' (not patented).
16. *Petal*.—Size: Medium, 1.0 cm in length 1.2 cm in width, similar to cultivar 'Robin' (not patented).
17. *Petals, the characteristics of the margins*.—Soft. 18. The texture of petals is smooth.
19. *The length of the pedicel*.—9-10 mm.
20. *The measurements of the nectaries*.—Absent.
21. *The presence of floral fragrance*.—Floral as 'Armking'.
22. *Petals*.—Number: five, similar to cultivar 'Redhaven' (not patented).
23. *Stamens*.—Position compared to petals: Above 0.5-1.0 mm, similar to cultivar 'Redhaven' (not patented).
24. *Stamens*.—Length: 0.5-0.6 mm, similar to cultivar 'Springtime' (not patented).
25. *Stamens*.—Color: yellow-orange color is classified as CIELab L=83.60 a=4.17 b=43.00; Mcguire R. G., 1992).
26. *Stigma*.—Position compared to anthers: Above, similar to cultivar 'Redhaven' (not patented).
27. *Anthers*.—In number 32 to 39, and the characteristic color is classified as CIELab L=83.13 a=4.21 b=43.43; Mcguire R. G., 1992). Pollen: Present, similar to cultivar 'Redhaven' (not patented).
28. *Pistil*.—Length: 0.5-0.6 mm, similar to cultivar 'Springtime' (not patented).
29. *Ovary*.—Pubescence: Absent, similar to cultivar 'Fuzalode' (not patented).
30. *Young shoot*.—Length of stipule (fully expanded leaf): Long, similar to cultivar 'Robin' (not patented).
31. *Number of the stipules*.—Two.
32. *Length of the stipules*.—7 mm.
33. *Color of the stipules*.—Yellowish green.

Mature leaf:

34. *Leaf arrangement*.—Alternate.
35. *The venation pattern*.—Brachidodrome, pinnate.
36. *The leaf color in upper surface of young leaves*.—Medium green similar to cultivar 'Robin', the objective color in CIELab coordinates is L=30.2 a=−6.99 b=8.05 (Mcguire R. G., 1992).

37. *The leaf color in lower surface of young leaves*.—Light green. The objective color in CIELab coordinates is L=37.79 a=−9.28 b=12.29 (Mcguire R. G., 1992).
38. *The leaf margins*.—Crenate, like cultivar 'Crimson Glo' (U.S. Plant Pat. No. 12,856).
39. *The texture of the leaf*.—Smooth
40. *Mature leaf blade*.—Length: Long, 13-15 cm.
41. *Mature leaf blade*.—Width: Medium, 3-4 cm.
42. *Mature leaf blade*.—Ratio length/width: Medium, 4.5, similar to cultivar 'Early Sungrand' (not patented).
43. *Mature leaf blade*.—Shape in cross section: Flat, similar to cultivar 'Mayred' (not patented).
44. *Mature leaf blade*.—Recurvature of apex: Absent, similar to cultivar 'Merril Sundance' (not patented).
45. *Mature leaf blade*.—Angle at base: Acute less than 60°, similar to cultivar 'Springtime' (not patented).
46. *Mature leaf blade*.—Angle at apex: Small, similar to cultivar 'Red June' (not patented).
47. *Mature leaf blade*.—Color: Green, similar to cultivar 'Robin' (not patented), classified as (CIELab: L=37.45 a=−8.20 b=−15.48; Mcguire R. G., 1992) on the upper surface and CIELab: L=58.31 a=−5.71 b=−12.55; Mcguire R. G., 1992, in the lower surface.
48. *Petiole of a mature leaf*.—Length: Medium 0.8-1.1 cm, similar to cultivar 'Genadix' (not patented).
49. *Petiole of a mature leaf*.—Nectaries present, similar to cultivar 'Redhaven' (not patented).
50. *Petiole of a mature leaf*.—Shape of nectaries: Reniform, similar to cultivar 'Redhaven' (not patented).
51. *Petiole of a mature leaf*.—Predominant number of nectarines: More than two, similar to cultivar 'Everts' (not patented).

Fruit:

52. *Fruit*.—Size: Large 190-240 g, similar to cultivar 'Loring' (not patented).
53. *Fruit*.—Shape (in ventral view): Round, similar to cultivar 'Redwing' (not patented).
54. *Fruit*.—Shape of pistil end: Weakly pointed, similar to cultivar 'Springtime' (not patented).
55. *Fruit*.—Symmetry (viewed from pistil end): Symmetric, similar to cultivar 'Morettini' (not patented).
56. *Fruit*.—Prominence of suture: Weak, similar to cultivar 'Redhaven' (not patented).
57. *Fruit*.—Depth of stalk cavity: Medium 0.7-1.2 cm.
58. *Fruit*.—Width of stalk cavity: Medium 1.2-1.4 cm.
59. *Fruit*.—Ground color: Yellow, similar to cultivar 'Fuzalode' (not patented), greenish yellow, classified as CIELab: L=62.16 a=5.18 b=29.45; Mcguire R. G., 1992.
60. *Fruit*.—Over color present, covering 60% of the fruit surface.
61. *Fruit*.—Hue of over color: Medium red, similar to cultivar 'Red Diamond' (not patented), classified as CIELab: L=29.34 a=57.55 b=27.12; Mcguire R. G., 1992.
62. *Fruit*.—Pattern of over color: Striped, similar to cultivar 'Veteran' (not patented).
63. *Fruit*.—Pubescence: Absent.
64. *Fruit*.—Thickness of skin: Medium, similar to cultivar 'Madame Girard' (not patented).
65. *Fruit*.—Adherence of skin to flesh: Strong, similar to cultivar 'Babygold5' (not patented).
66. *Fruit*.—Firmness of pulp: Firm 8.6-16.2 pounds, similar to cultivar 'Redhaven' (not patented).
67. *Fruit*.—Ground color of flesh: Yellow, classified as CIELab L=63.44 a=4.57 b=21.29; Mcguire R. G., 1992.
68. *Fruit*.—Anthocyanin coloration directly under skin: Weakly expressed.
69. *Fruit*.—Anthocyanin coloration of flesh: Absent.
70. *Fruit*.—Anthocyanin coloration around stone: Strongly expressed.
71. *Fruit*.—Texture of the flesh: Not fibrous, similar to cultivar 'Redhaven' (not patented).
72. *Fruit*.—Sweetness: High 13.4-16.1 Brix %, similar to cultivar 'Philip cling' (not patented).
73. *Fruit*.—Acidity: High 0.85-1.0%, similar to cultivar 'Armking' (not patented).
74. *Average size of the fruit*.—Large, like cultivar 'Loring', reaching 212 gr.
75. *The aroma of the fruit*.—Average as 'Venus'.

Stone:

76. *Stone*.—Size compared to fruit: Medium 3.5-4.0 cm long and 2.0-2.2 cm width, similar to cultivar 'Redhaven' (not patented).
77. *Stone*.—Shape (in lateral view): Elliptical, similar to cultivar 'Loring' (not patented).
78. *Stone*.—Intensity of brown color: Dark, CIELab L=27.67 a=16.21 b=7.66; Mcguire R. G., 1992.
79. *Stone*.—Relief of surface: pit similar to cultivar 'Madame Girard' (not patented).
80. *Stone*.—Tendency of splitting (at peak harvest): Absent or very low, similar to cultivar 'Fairhaven' (not patented).
81. *Stone*.—Adherence to flesh: Present, similar to cultivar 'Sweet Gold' (not patented).
82. *Stone*.—Degree of adherence to flesh: Medium, similar to cultivar 'Spring Crest' (not patented).

Phenology:

83. *Time of leaf bud burst*.—Early, similar to cultivar 'Springtime' (not patented). In the Southern Hemisphere is between $9^{th}$ to $12^{th}$ September.
84. *Time of beginning of flowering*.—Medium, similar to cultivar 'Redhaven' (not patented). In the Southern Hemisphere is between $10^{th}$ to $18^{th}$ August.
85. *Duration of flowering*.—Medium, similar to cultivar 'Redhaven' (not patented), 6-8 days.
86. *Time of maturity for consumption*.—Late, similar to cultivar 'Veteran' (not patented). In the Southern Hemisphere is on February $28^{th}$ to March $4^{th}$.
87. *Tendency to preharvest*.—Absent, similar to cultivar 'Redhaven' (not patented).
88. *Pest/disease resistance/susceptibility*.—This genotype is not genetically resistant to any common pest and disease of peach, as Mildew, leaf curl, bacterial canker, aphids, thrips or, Oriental moth. 89. Productivity is high, reaching 30 to 40 Tons per hectare in the fifth year. 90. Fruit characterization is on table 1.

TABLE 1

Fruit characterization of the nectarine cultivar 'Andes Nec-2'.

| | Skin Blush | Ecuatorial Diameter | Firmness (pounds) | | | Soluble solids |
|---|---|---|---|---|---|---|
| Season | (%) | (cm) | Shoulders | Suture | Tip | (° Brix) |
| 2009-2010 | 60 | 10.2 | 8.6 | 9.7 | 10.4 | 13.4 |
| 2010-2011 | 60 | 12.3 | 11.0 | 12.5 | 12.8 | 16.1 |
| 2011-2012 | 50 | 16.2 | 11.9 | 15.0 | 16.0 | 13.8 |

Postharvest behavior: At 50 days in cold storage +3 days at ambient temperature has good external appearance, no browning color or mealy texture, good taste and flesh firmness.

General technical notes: Very good outward appearance. Excellent color coverage. Fruit round, no tip. High productivity. Good flavor. Andes Nec-2 is a full self-fertile variety. No pollinator is needed for proper fruit production.

Conclusions: After five years of evaluation, the variety continues to show its outstanding characteristics: very good productivity, good size, good flavor and good external appearance (some skin russet). High potential for export purposes because of exceptional post-harvest life.

Having thus described and illustrated the new variety of nectarine tree, I claim:

1. A new and distinct variety of nectarine tree, substantially as illustrated and described, that is similar to 'August Red' nectarine by producing nectarines that mature at the end of the harvest season, yellow flesh, clingstone in type, and firm in texture, but is distinguished therefrom by maturing a week after, and by producing fruit with a better and longer postharvest potential.

* * * * *